(12) United States Patent
Lagendijk et al.

(10) Patent No.: US 7,306,557 B2
(45) Date of Patent: Dec. 11, 2007

(54) DEVICE FOR IMAGE GUIDED AUTOMATED INSERTION OF AN ELONGATED HOLLOW NEEDLE TO A DESIRED LOCATION IN AN ANIMAL BODY FOR EFFECTING RADIATION THERAPY OF CANCEROUS TISSUE

(75) Inventors: Jan Jacob Wouter Lagendijk, Linschoten (NL); Marinus Adriaan Moerland, Duurstede (NL)

(73) Assignee: Nucletron B.V., Veenendaal (NL)

( * ) Notice: Subject to any disclaimer, the term of this patent is extended or adjusted under 35 U.S.C. 154(b) by 780 days.

(21) Appl. No.: 10/727,627

(22) Filed: Dec. 5, 2003

(65) Prior Publication Data

US 2004/0147836 A1 Jul. 29, 2004

(30) Foreign Application Priority Data

Jan. 27, 2003 (EP) .................................. 03075257

(51) Int. Cl.
*A61M 36/00* (2006.01)
(52) U.S. Cl. ......................................................... 600/7
(58) Field of Classification Search ................. 600/1–8, 600/407, 411, 424, 437
See application file for complete search history.

(56) References Cited

U.S. PATENT DOCUMENTS

| | | | | |
|---|---|---|---|---|
| 5,342,283 | A | * | 8/1994 | Good ............................ 600/8 |
| 6,241,670 | B1 | * | 6/2001 | Nambu ....................... 600/427 |
| 6,270,472 | B1 | * | 8/2001 | Antaki et al. ................. 604/61 |
| 6,311,084 | B1 | | 10/2001 | Cormack et al. |
| 6,398,711 | B1 | * | 6/2002 | Green et al. .................... 600/7 |
| 2002/0120175 | A1 | * | 8/2002 | Luth ............................. 600/7 |
| 2002/0143229 | A1 | | 10/2002 | Green et al. |
| 2003/0018232 | A1 | | 1/2003 | Elliot et al. |
| 2003/0139642 | A1 | * | 7/2003 | Hogendijk et al. ............ 600/7 |

FOREIGN PATENT DOCUMENTS

EP 1 070 519 A1 1/2001

\* cited by examiner

*Primary Examiner*—Samuel G. Gilbert
(74) *Attorney, Agent, or Firm*—Birch, Stewart, Kolasch & Birch, LLP

(57) ABSTRACT

The invention relates to a device for image guided automated insertion of an elongated an elongated hollow needle to a desired location in an animal body for effecting radiation therapy of cancerous tissue in said body comprising needle positioning means for positioning said needle having a distal end and a proximal end relative to said desired location; needle drive means for driving said needle with its distal end towards said desired location; and real time imaging means for creating and presenting an image of said desired location and the position of the distal end of said needle during insertion of said needle.

It is an object of the invention to provide a device for inserting a needle in an animal body, wherein a better access to the treatment site in the patient's body is obtained thus improving the possibilities in configuring a treatment plan for said patient and wherein the patient is suffering lesser trauma, bleeding and discomfort.

According to the invention these objects are met as the device is arranged for performing subsequent insertions using only one single needle, wherein the needle drive means are arranged for retracting said single needle from said desired location, and wherein said needle positioning means are arranged for repositioning said single needle relative to a subsequent desired location prior to a subsequent insertion.

17 Claims, 4 Drawing Sheets

DEVICE FOR IMAGE GUIDED AUTOMATED INSERTION OF AN ELONGATED HOLLOW NEEDLE TO A DESIRED LOCATION IN AN ANIMAL BODY FOR EFFECTING RADIATION THERAPY OF CANCEROUS TISSUE

This Nonprovisional application claims priority under 35 U.S.C. § 119(a) on Patent Application No(s). 03075257.0 filed in Europe on Jan. 27, 2003, the entire contents of which are hereby incorporated by reference.

The invention relates to a device for image guided automated insertion of an elongated an elongated hollow needle to a desired location in an animal body for effecting radiation therapy of cancerous tissue in said body comprising needle positioning means for positioning said needle having a distal end and a proximal end relative to said desired location; needle drive means for driving said needle with its distal end towards said desired location; and real time imaging means for creating and presenting an image of said desired location and the position of the distal end of said needle during insertion of said needle.

It is noted that the device and method according to the invention as described in this application can be used for each medical application, wherein a needle is to be inserted into an animal body using imaging means. For example, the device and method described in this patent application can be used as biopsy devices, and for any other devices wherein High Dose Radiation, Pulse Dose Radiation or Low Dose Radiation therapy is applied to an animal body, for example the radioactive seed implant treatment of prostate cancer.

There are different treatment methods for treating prostate cancer, like radical prostatectomy (surgery), external radiation by means of high energy electromagnetic beams and radioactive seed implantation. Radical prostatectomy has historically been very effective, but also has a relatively high rate of impotence, incontinence and surgical morbidity associated with it. External beam radiation has been reasonably effective for treatment of early stages of prostate cancer and has fewer side affects than radical prostatectomy. Beyond the early stages of the disease, however, external beam radiation decreases in effectiveness relative to the surgical procedure.

The third technique, radioactive seed implantation, involves the placement of radioactive seed-like elements in the prostate gland. The radioactive seeds deliver high dosages of radiation to the prostate, but relatively low dosages to the surrounding tissue, such that the radiation is quite targeted to the prostate, resulting in the destruction of cancer cells in the prostate before they can spread to other parts of the body.

An example of radioactive seed implant treatment of prostate cancer according to the introduction above is for example disclosed in the European patent application no. EP-A1-1 070 519 filed by the same applicant. With this technique, also known as brachytherapy, it is possible to treat a patient outdoors instead of at the hospital and the patient can resume his normal activities just a couple of days after the treatment. The technique has proven to have relatively low incontinence and impotency rates and therefore has become increasingly attractive, and has become more implemented than surgery (radical prostatectomy).

With the device and method according to EP-A1-1 070 519 hollow needles are inserted to a desired location in the prostate gland under guidance of real time imaging means, e.g. ultrasound using an ultrasound probe, which probe is introduced into the rectum. A more accurate position of the needles can be obtained by using positioning means comprising a template provided with a plurality of guiding holes for the implant needles. Once the hollow needles are inserted at their desired locations in the prostate gland radioactive seeds are inserted into said hollow needles. The number and relative positions of said seeds are determined and calculated in accordance with a preplanned dosimetry pattern using a doses planning therapy system.

Once the radioactive seeds are implanted into the hollow needles, said needles are retracted from the body leaving the implanted seeds in the prostate gland for radiating the cancer cell by means of natural radioactive decay.

A drawback of said technique can be found in the large number of hollow needles, which are all implanted at a different locations in the patient's body. These needles remain a certain time span inside the patient's body as the needles are connected one after another with a so-called after loading apparatus for inserting the radioactive seeds into each needle. Each needle generates an implant wound and as the number of implant needle can be 20 or more the patient is thus suffering a lot of trauma, bleeding and discomfort.

A further drawback is the limited space between the legs of the patient and the limited access to the prostate due to the presence of e.g. the symphysis limiting the dimensions of the template used resulting in less flexibility in configuring a treatment plan for the radiation therapy to be effected.

It is therefore an object of the invention to provide a device and method for automated insertion a needle in an animal body for effecting radiation therapy in said body, wherein a better access to the treatment site in the patient's body is obtained thus improving the possibilities in configuring a treatment plan for said patient.

It is another object of the invention to provide a device and method for inserting a needle in an animal body for effecting radiation therapy in said body, wherein the patient is suffering lesser trauma, bleeding and discomfort.

According to the invention these objects are met as the device is arranged for performing subsequent insertions using only one single needle, wherein the needle drive means are arranged for retracting said single needle from said desired location, and wherein said needle positioning means are arranged for repositioning said single needle relative to a subsequent desired location prior to a subsequent insertion.

The use of a large number of needles as well as a template as positioning means with evidently large dimensions is no longer required with the present invention, as the use of only one single needle for subsequent insertions allows a more efficient use of the space near the treatment site of the patient and more in particular between the legs of a male patient when treating prostate cancer.

Moreover the use of only one single needle results in a smaller amount of implant wounds, less trauma, bleeding and discomfort to the patient.

A further improvement of the device according to the invention wherein the number of implant wounds is further reduced to one or two is characterized in that for repositioning said single needle between subsequent insertions said retracted distal end of the needle is pivoted around at least one pivoting point. Possibly said pivoting point is located inside or outside said animal body or located at skin level of said animal body.

For a proper orientation and positioning of the single needle near the treatment site of the patient's body said needle positioning means comprise a guidance channel having a proximal end and distal end for accommodating said single needle.

More in particular said needle positioning means comprise a robotic system connected to said guidance channel. The use of a robotic system allows an accurate and versatile orientation of the single hollow needle in nearly any orientation relative to the patient's body and the intended site to be treated.

Furthermore this spatial construction requires less space near the patient's body thus allowing a more versatile configuration of the radiation treatment plan to be effected.

Preferably said single elongated hollow needle is made of a non-ferromagnetic material, for example of a titanium-zirconium alloy, in case of MRI imaging.

In another advantageous embodiment the proximal end of said single elongated hollow needle is connected to an after loading apparatus and more in particular said proximal end of said single elongated hollow needle is connected to an after loading apparatus by means of a flexible catheter tube. In a further embodiment said after loading apparatus is connected to said robotic system.

Said after loading apparatus can be for example a radioactive seed loading apparatus, or the after loading device is a HDR, PDR or LDR-device.

Moreover said single elongated hollow needle may have an open distal end allowing the implant of one or more energy emitting sources in the patient's body in a permanent manner, that is the implant of e.g. radioactive seeds, which seeds remain in the patient body (e.g. at a specific location inside the male prostate) after the retraction of the single needle.

Also said single elongated hollow needle may have a closed distal end in another embodiment, allowing a temporarily implant of an energy emitting source (e.g. a High, Pulse of Low Dose Radiation source) near the distal end inside the hollow needle and inside the patient's body. Once the energy emitting source has remained for a certain amount of time at said location within the patient's body, the energy emitting source is retracted from the hollow needle, which needle is subsequently retracted for a subsequent insertion, now towards another location within the patient's body for a subsequent radiation treatment session with the same energy emitting source.

In further embodiment of the device according to the invention the real time imaging means can be ultrasound imaging means, magnetic resonance imaging (MRI) means or computer tomography (CT) imaging means.

The invention will now be described in more detail with reference to a drawing, which drawing shows:

It is to be noted that the following detailed description will be made with respect to treatment of a prostate gland. However, the device and method according to the invention can be used for each medical application, wherein a needle is to be inserted into an animal body using imaging means. The device and method described in this patent application can also be used as biopsy devices, and in far more applications wherein High Doses Radiation or Low Doses Radiation therapy is applied to an animal body. Therefore the description below should be regarded as an illustration for one specific application and not as a limitation of the invention.

Figure 1:
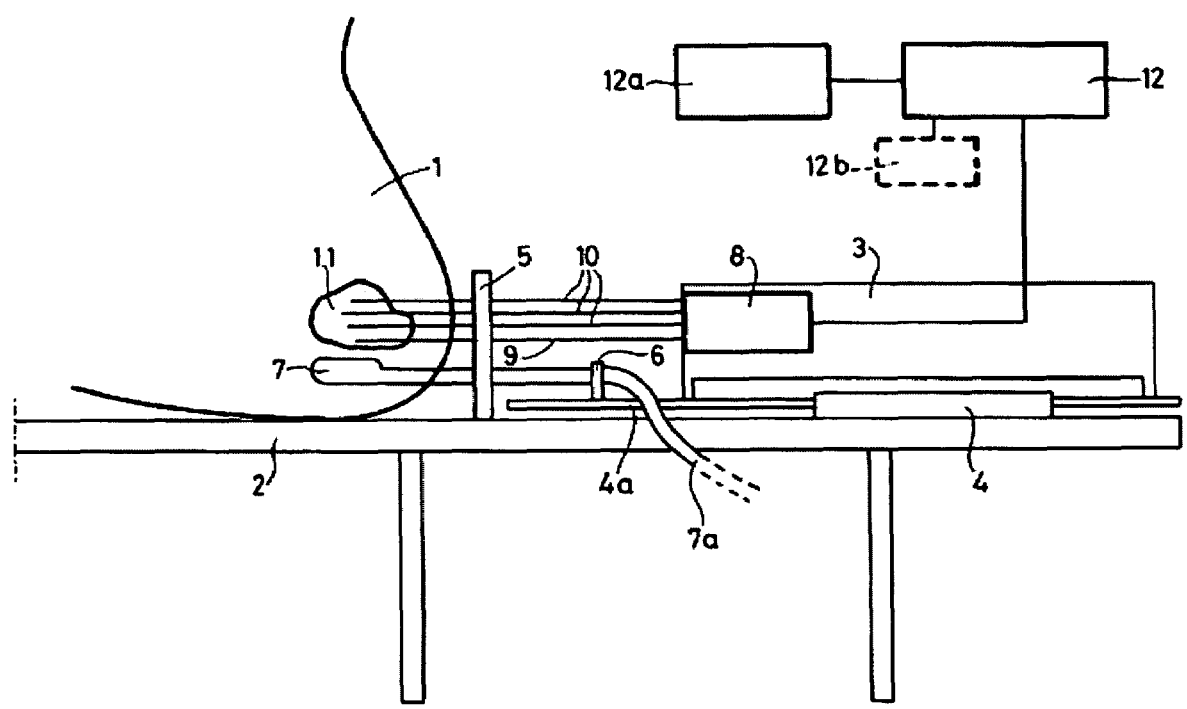
FIG. 1 shows a schematic and simplified device according to the state of the art.

FIG. 1 shows in very schematic form various elements of a known device for implanting radioactive seeds into a prostate gland. A patient 1 is shown lying in lithotomy position on a table 2. Fixedly connected to the table 2 is a housing 3. Housing 3 comprises a drive means 4 to move rod 4a stepwise. A template 5 is connected or mounted to the table 2, which template is provided (not shown) with a plurality of guiding holes through which holes hollow needles 9, 10 can be positioned relative to the patient. By means of a holder 6 a transeptal imaging probe 7 is fixedly connected to said rod 4a, which is moveable in a direction towards and from the patient by means of the drive means 4. The imaging probe 7 can be an ultrasound probe.

A needle 9 is used for fixing the prostate gland 11 in position relative to the template 5. A number of needles 10 is fixed into position through the template 5 in the prostate gland 11. The template 5 determines the relative positions of the needles 10 in two dimensions. The needles 10 are open at their distal ends and are sealed of by a plug of biocompatible, preferably bio-absorbable wax. In said housing 3 a seed loading unit 8 is present.

A well-known therapy planning module 12a is provided for determining the number and relative positions of seeds in each needle for implantation in the prostate gland 11. Such therapy planning module 12a usually comprises a computer programmed with a therapy planning program. The therapy planning module 12a is connected to the seed loading unit 8 through a control device 12 for controlling the number of seeds for each needle. Control device 12 may be a separate device or may be an integrated part either of the seed loading unit 8 or of the therapy planning module 12a or may be embodied in the software of the therapy planning module 12a or of the seed loading unit 8.

The known device shown in FIG. 1 operates as follows. A patient 1 is under spinal or general anaesthesia and lies on the operating table 2 in lithotomy position. The (ultrasound) imaging probe 7 is introduced into the rectum and the probe is connected via signal line 7a with a well known image screen, where an image may be seen of the inside of the patient in particular of the prostate gland 11 as seen from the point of view of the imaging probe 7. The template 5 is attached to the drive means 4, thereby insuring the correlation of the ultrasound image geometry and the template 5. The prostate gland 11 is fixed relative to the template 5 and the drive means 4 and the imaging probe 7 by means of one or more needles 9, 10. Subsequently further needles 10 are introduced in the body and the prostate gland under ultrasound guidance one by one.

Moving the imaging probe with the drive means 4 longitudinally within the rectum controls the needle depths of each needle 10. After all needles 10 have been placed, their positions relative to the prostate gland 11 are determined in at least one of several known ways. In a known way the therapy planning module 12a determines how the needles 10 are to be placed in the prostate and how many radioactive seeds are to be placed in what order in each of the needles 10. The information about the desired placement of the radioactive seeds in the needles 10 is used to control the seed loading unit 8.

Usually the seeds are spaced from each other by spacers. For example seeds of 0.5 cm length may be spaced by spacers also of 0.5 cm length. Other measures of seeds and spacers are imaginable. A set of seeds and spacers loaded or to be loaded into a needle will be called a seed train or a train of seeds or a seed-spacer train. For each needle 10 the configuration of an applicable seed-spacer train is determined by the therapy planning module 12a. The seed loading unit 8 is controlled by the control device 12 to make up a seed-spacer train for each needle 10. Once a seed-spacer train is to be or has been made up for a specific needle a connection is made to the specific needle. After the seed-spacer train has been made up it is urged into the specific needle by a pushing drive (not shown) that is part of the seed loading unit 8.

Since all elements of the seed loading unit 8 and the needles 10 and their interconnections are of specific pre-known dimensions, which may or may not be the same for all like elements and such dimensions have been made known, e.g. pre-loaded in or pre-entered via a keyboard 12b to the control device 12 the pushing drive pushes with a pushing wire the seed-spacer train just until it reaches the distal end of the specific needle. Subsequently the pushing wire is fixed in position and the specific needle is retracted over a distance equal to or slightly greater than the length of the seed-spacer train in it. Thereby the wax plug and the seed-spacer train are introduced in the prostate gland 11.

Next the pushing wire is withdrawn into the seed loading unit 8 for pushing a next seed-spacer train into the prostate gland 11. The delivery of seed-spacer trains in the prostate gland continues until each needle 10 has been retracted and a number of seed-spacer trains equal to the number of needles 10 has been delivered in the prostate gland 11. Subsequently the needles 10 are retracted from the patient completely. After the geometry of the implanted seeds has been checked under fluoroscopy or another method of checking the presence of the seeds in the prostate gland 11 and removal of the ultrasound probe 7 the patient 1 is hospitalized for recovery.

As clearly disclosed in FIG. 1 a major drawback of this implant technique can be found in the large number of hollow needles or stylets, which are all implanted at a different locations in the patient's body. These needles remain a certain time span inside the patient's body as the needles are connected one after another with the after loading apparatus for inserting the radioactive seeds into each needle. Each needle generates an implant wound and as the number of implant needles can be 20 or more the patient is thus suffering a lot of trauma, bleeding and discomfort.

A further drawback is the limited space between the legs of the patient and the limited access to the prostate due to the presence of e.g. the symphysis limiting the dimensions of the template used resulting in less flexibility in configuring a treatment plan for the radiation therapy to be effected.

Yet another drawback of the methods presently used, is that the hollow needles are inserted manually by the medic personnel. This latter drawback is obviated with the device according to the present invention.

Figure 2:
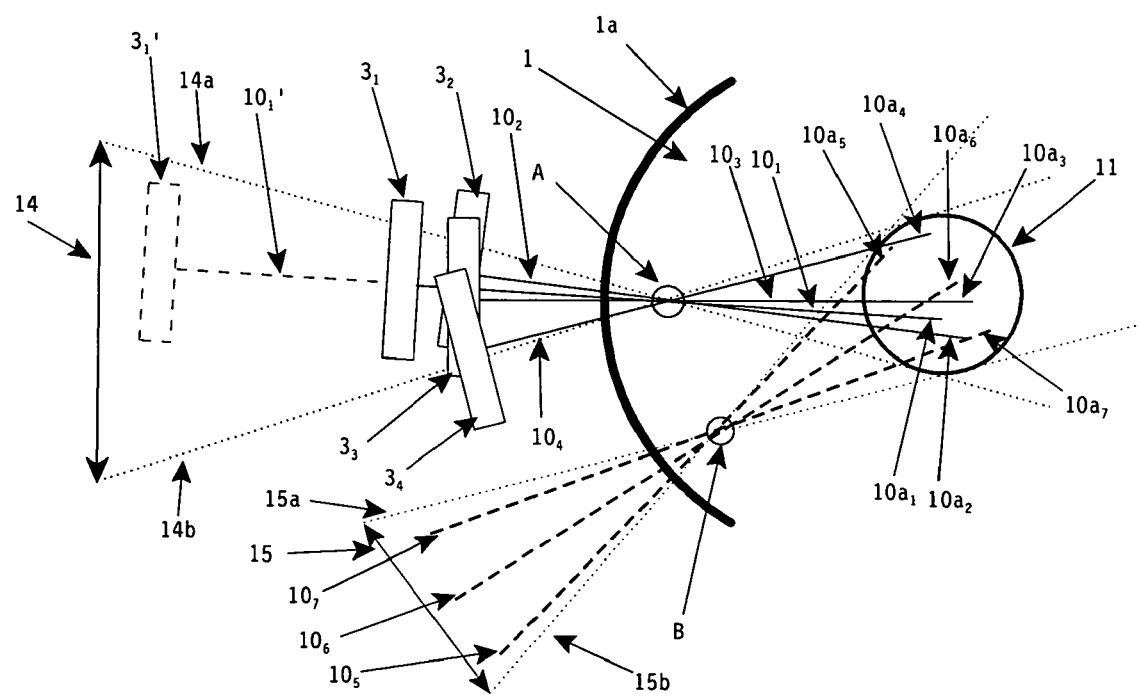
FIG. 2 shows the principle of the invention.

FIG. 2 discloses the principle of the present invention, which principle obviates the drawbacks of the known insertion devices according to the state of the art.

Also in this drawing reference numeral 1 depicts the body of a patient, whereas the prostate gland 11 is schematically depicted by means of a circle. The principle of the present invention uses only one single needle for performing subsequent insertions into the patient's body 1 towards a desired location within the prostate gland 11 to be treated. To this end, between subsequent insertions said single implant needle 10 can be repositioned using suitable needle positioning means (not depicted in FIG. 2) relative to a subsequent desired location.

After each insertion the needle drive means 3 are arranged for retracting said single needle 10 from its initial location within the prostate gland 11 and the needle positioning means reposition said needle 10 together with the needle insertion means 3 relative to a new subsequent location relative to the patient's body 1 and the prostate gland 11. After repositioning the needle insertion means 3 subsequently insert said needle 10 towards its new desired location within the prostate gland 11.

The principle will now be described in more detail refering to FIG. 2. Prior to the radiation treatment session, the whole device (here depicted schematically in broken lines by means of the needle drive means $3_1'$ and said single hollow needle $10_1'$) is positioned between the legs of a male patient and said single hollow needle $10_1'$ is positioned by suitable needle positioning means (not shown) relative to a desired location within the prostate gland 11. Subsequently said needle drive means $3_1$ drive said needle $10_1$ through the skin 1a into the patient's body 1 towards a desired location within the prostate gland 11, which desired location is depicted with the distal end $10a_1$ in FIG. 2.

Once the needle $10_1$ has been inserted into position through said hollow needle $10_1$ suitable energy emitting sources may be introduced towards the distal end $10a_1$. These energy emitting sources can be radioactive seeds which are to be implanted permanently within the prostate gland 11 at said location $10a_1$ or said energy emitting source can be implanted temporarily during a certain time span for effecting a radiation treatment.

In the first treatment example the hollow needle $10_1$ is retracted leaving the implanted radio active seeds at the desired location $10a_1$ within the prostate gland 11.

In the second treatment example the hollow needle $10_1$ remains in place during the time span of the radiation treatment session to be effected and is then retracted after the retraction of the energy emitting source back towards for example an afterloading device or seed loading device, which apparatuses are connected with the single hollow needle $10_1$ (not shown in FIG. 2).

In both situations the hollow needle $10_1$ is retracted and subsequently repositioned relative to a new desired location as determined by the pre-planning system within the prostate gland 11. During repositioning the distal end 10a of the hollow needle 10 is maintained by the needle positioning means at one position, such that the needle 10 is pivoted around said pivoting point. Said pivoting point is depicted with reference numeral A in FIG. 2.

After repositioning the hollow needle 10 and the insertion means 3 are now in a new insertion position (now depicted with reference numerals $3_2$ and $10_2$) and the needle drive means $3_2$ insert the needle $10_2$ towards a new location within the prostate gland, until the distal end $10a_2$ reaches said desired location.

Again, radioactive seeds are to be implanted permanently or an energy emitting source is to be implanted temporarily through the hollow needle $10_2$ towards the new location, here depicted with reference numeral $10a_2$.

Likewise, for each subsequent position within the prostate gland 11 (indicated with reference numerals $10a_3$ and $10a_4$) the hollow needle 10 is retracted by the needle insertion means 3 until the distal end 10a arrives at the pivoting point A. Then the needle positioning means reposition the needle insertion means 3 and the single hollow needle 10 relative to a new location in the patient's body (for example new position $3_3$-$10_3$ or $3_4$-$10_4$) and the hollow needle $10_3$ ($10_4$) is inserted toward said subsequent position within the prostate gland 11, until the distal end 10a arive at the new location 10$a_3$ (10$a_4$).

Using suitable imaging means as described above in relation with FIG. 1 the exact location of the distal end 10a of the needle within the patient's body can be monitored and the needle drive means 3 can be deactivated at the time the distal end 10a reaches its predetermined position within the prostate gland 11.

Likewise the imaging means are used for monitoring the retraction of the needle 10 prior to a subsequent insertion and to monitor whether the distal end 10a of the needle 10 is properly retracted until the imaginary pivoting point A.

It will be appreciated when that with this new insertion technique wherein only one single needle is used, and wherein the needle is repositioned for each subsequent insertion such that the needle 10 is pivoted around at least one pivoting point A maintaining the distal end 10a in that pivoting point results in a fewer amount of insertion wounds at skin level 1a, as the hollow needle 10 is inserted towards each subsequent location within the prostate gland 11 through the same insertion wound. Thus the patient is suffering less trauma, bleeding and discomfort.

Moreover, with this technique a better access to the treatment site near the patient's body 1 is obtained thus improving the possibilities (treatment locations of the needle 10) in configuring a radiation treatment plan for said patient.

Furthermore, unlike with the known treatment techniques this single needle remains only a short period of time inside the patient's body at a specific location, as the single needle is continuously connected with the after loading apparatus for inserting radioactive seeds towards said specific location.

Also the single needle is inserted under automated imaging guidance, whereas with the methods presently used the hollow needles are inserted manually by the medic personnel. This significantly improves the accuracy of the device according to the invention.

In certain cases it is possible to relocate the whole device relative to the patient's body 1 and to perform a new series of subsequent insertions. In that situation the pivoting point of the needle 10 is now shifted to another location within the patient's body 1, for example depicted in FIG. 2 with reference numeral B.

Thus, as with the insertion device according to the state of the art a template is used for implanting a large number of needles (e.g. 20) resulting in a number of implant wounds at skin level 1a equal to the number of needles used the patient will suffer a lot of trauma, bleeding and discomfort, according to the insertion principle of the present invention only one or two (depending on the radiation treatment plan to be effected for the patient) insertion wounds have to be made, significantly reducing the trauma, bleeding and discomfort for the patient.

Preferably, each pivoting point A and B is located at skin level 1a resulting in a small implant wound, as the needle 10 will be inserted through the same implant wound after each repositioning procedure. It is also possible to locate the pivoting points A and B just outside the patient's body 1 near-skin level 1a or, as shown in FIG. 2, just below skin level 1a within the patient's body 1.

Figure 3:
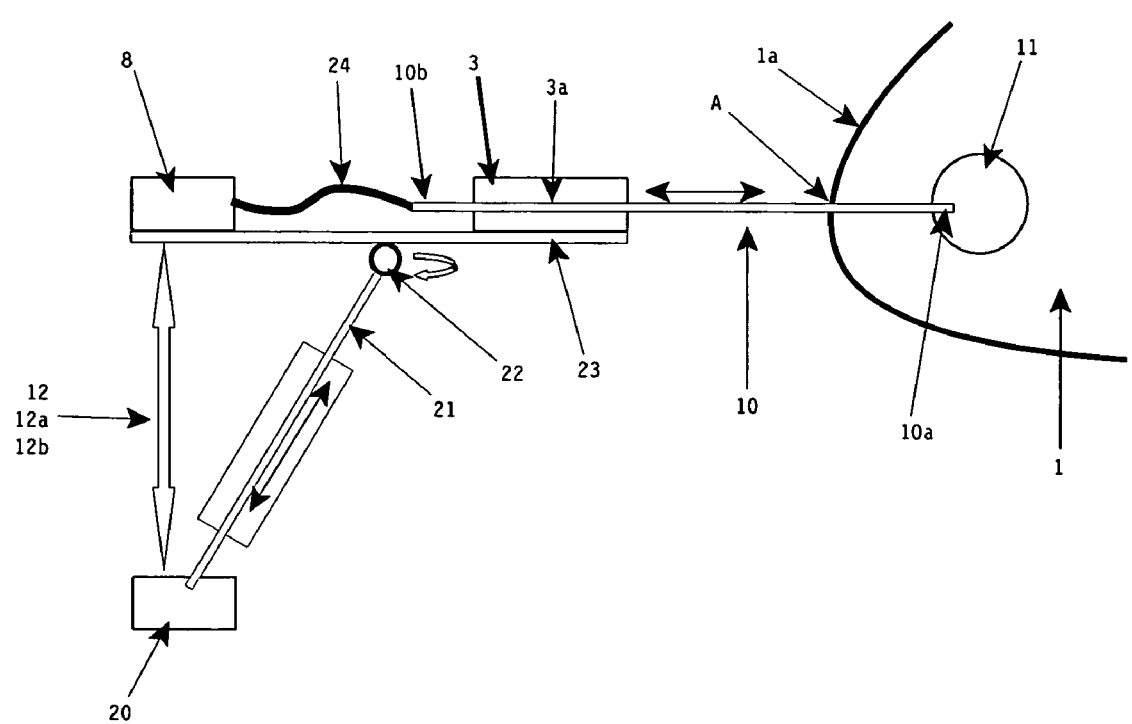
FIG. 3 shows a schematic view of a first embodiment of a device according to the invention.
Figure 4:
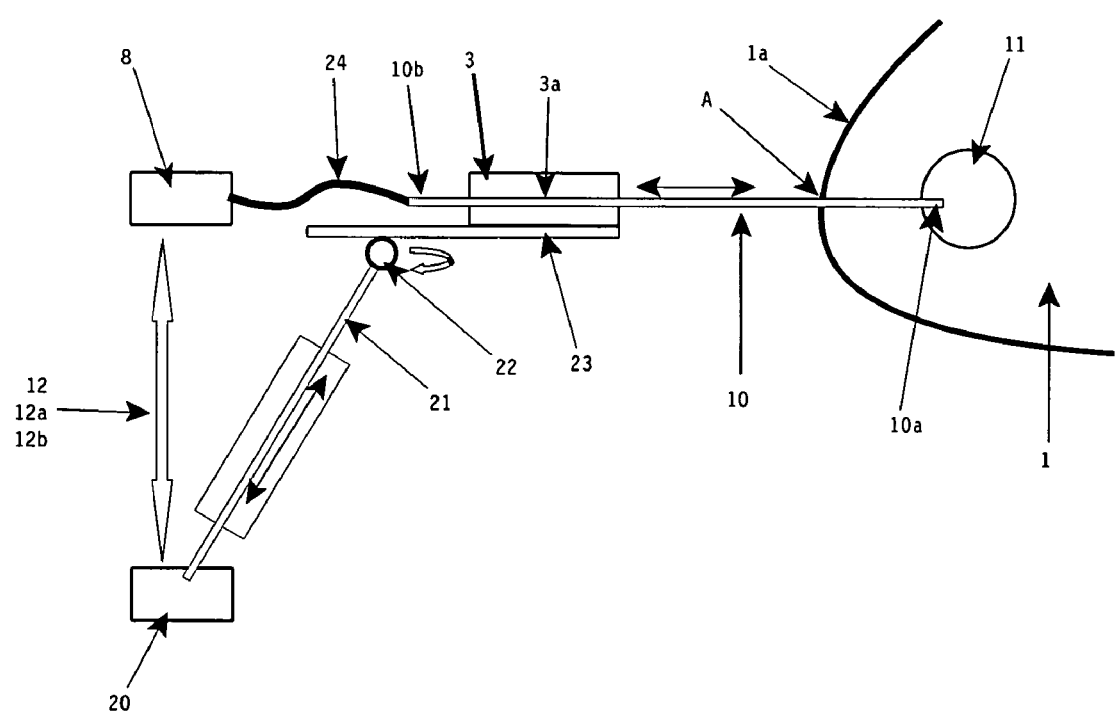
FIG. 4 shows a schematic view of a second embodiment of a device according to the invention.

In FIGS. 3 and 4 a first and second embodiment of an insertion device according to the invention are shown. In both Figures corresponding parts are depicted with the same reference numerals.

For repositioning the single hollow needle 10 (as shown in FIG. 2) toward a new subsequent desired location within the prostate gland 11 the device as shown in FIGS. 3 and 4 comprise needle positioning means 20 having a robotic system 21, which robotic system 21 is connected to a mounting plate 23 via a joint 22, e.g. a ball joint.

To the mounting plate 23 are the needle insertion means 3 mounted, which needle insertion means 3 comprise a guidance channel 3a through which the single hollow needle 10 is guided.

The needle positioning means 20 are arranged for displacing the robotic system 21 in a longitudinal direction depicted with the double arrow as well as rotating the robotic system 21 in a direction depicted by the circular arrow. Both transversal/longitudinal and rotational displacements of the robotic system 21 result in a re-orientation of the mounting plate 23 and the needle insertion means 3 as well as the hollow needle 10 relative to the patient's body 1.

As the hollow needle 10 is retracted by the needle insertion means 3 prior to each repositioning, the hollow needle 10 is pivoted around a pivoting point. During repositioning the distal end 10a is maintained in said pivoting point by the needle positioning means 20.

As this pivoting point is preferably located at skin level 1a, this insertion technique generates only one insertion wound depicted with A in FIG. 3 and FIG. 4.

The proximal end 10b of the hollow needle 10 is connected with for example an afterloading apparatus 8 by means of a flexible catheter tube 24. Once the single hollow needle 10 is inserted at a desired location within the prostate gland 11, radioactive seeds or an energy emitting source are to be inserted from said afterloading apparatus 8 through said flexible catheter tube 24 and the hollow needle 10 towards the intended location within the prostate gland 11 as depicted by the location of the distal end 10a.

After each insertion and the permanent implant of radioactive seeds or the temporarily implant of an energy emitting source the hollow needle 10 is retracted until the distal end 10a arrives at the pivoting point A. Subsequently, the needle positioning means 20 activate the robotic system 21 in order to reposition the needle insertion means 3 and the hollow needle 10 relative to a new desired location within the patient's body 1. This repositioning is based on radiation treatment planning parameters 12a-12b as prepared and calculated in accordance with a preplanned dosimetry pattern using a doses planning therapy system 12 as shown in FIG. 1. This doses planning therapy system 12 also controls the afterloading apparatus 8 for inserting the radioactive implant seeds within the patient's body 1.

In a preferred embodiment the robotic system 21 may include the control system of the afterloading apparatus 8 resulting in a compact and sophisticated device with limited dimensions, which device can be easily positioned between the legs of a male patient.

In FIG. 3 the afterloading apparatus 8 is mounted together with the needle insertion means 3 to the mounting plate 23, which plate is likewise connected via the joint 22 to the robotic system 21. Thus, in the embodiment as disclosed in FIG. 3, the needle positioning means 20 reposition via the robotic system 21 the mounting plate 23 together with the afterloading apparatus 8, the needle insertion means 3 and the single hollow needle 10. This construction leads to a compact device with limited dimensions which can be easily positioned between the legs of a male patient.

Another embodiment is disclosed in FIG. 4 wherein the afterloading apparatus 8 is placed at some distance from the patient, whereas the mounting plate 23 only supports the needle insertion means 3 with the guidance channel 3a in which the single hollow needle 10 is accommodated. The assembly of the mounting plate 23, the needle insertion means 3 and the single hollow needle 10 is connected via the joint 22 to the robotic system 21.

It will be appreciated that this new insertion technique not only allows a more efficient use of the limited space between the legs of the patient and the limited access to the prostate gland 11, but it also reduces the amount of insertion wounds significantly. When proper and accurate subsequent insertion procedures are performed, the number of insertion wounds can be minimized to one or two wounds, significantly limiting the amount of trauma, bleeding and discomfort to the male patient.

The invention claimed is:

1. Device for image guided automated insertion of an elongated hollow needle to a desired location in an animal body for effecting radiation therapy of cancerous tissue in said body comprising:
   needle positioning means for positioning said needle having a distal end and a proximal end relative to said desired location;
   needle drive means for driving said needle with its distal end towards said desired location; and
   real time imaging means for creating and presenting an image of said desired location and the position of the distal end of said needle during insertion of said needle; wherein
   the device is arranged for performing subsequent insertions using only one single needle, wherein
   the needle drive means are arranged for retracting said single needle from said desired location until the distal end of said needle arrives at a pivoting point, and wherein
   said needle positioning means are arranged for repositioning said single needle relative to a subsequent desired location prior to a subsequent insertion by pivoting said needle around said pivoting point while said distal end of said needle is maintained in the pivoting point.

2. A device according to claim 1, wherein said pivoting point is located inside said animal body.

3. A device according to claim 1, wherein said pivoting point is located outside said animal body.

4. A device according to claim 1, wherein said pivoting point is located at skin level of said animal body.

5. A device according to claim 4, wherein said needle insertion means comprise a guidance channel having a proximal end and distal end for accommodating said single needle.

6. A device according to claim 5, wherein said needle positioning means comprise a robotic system connected to said guidance channel.

7. A device according to claim 1, wherein the proximal end of said single elongated hollow needle is connected to an after loading apparatus.

8. A device according to claim 7, wherein the proximal end of said single elongated hollow needle is connected to an after loading apparatus by means of a flexible catheter tube.

9. A device according to claim 7, wherein the after loading device is a radioactive seed loading apparatus, a HDR, PDR or LDR-device.

10. A device according to claim 7, wherein the after loading device is connected to the robotic system of the needle positioning means.

11. A device according to claim 1, wherein said single elongated hollow needle has an open distal end.

12. A device according to claim 1, wherein said single elongated hollow needle has a closed distal end.

13. A device according to claim 1, wherein said single elongated hollow needle is made of a non-ferromagnetic material.

14. A device according to claim 13, wherein said non-ferromagnetic material is a titanium-zirconium alloy.

15. A device according to claim 1, wherein the real time imaging means are ultrasound imaging means.

16. A device according to claim 1, wherein the real time imaging means are magnetic resonance imaging means.

17. A device according to claim 1, wherein the real time imaging means are computer tomography imaging means.

* * * * *